US008449175B2

(12) United States Patent
Plotnikov et al.

(10) Patent No.: US 8,449,175 B2
(45) Date of Patent: May 28, 2013

(54) ISOTHERMAL TITRATION MICROCALORIMETER APPARATUS AND METHOD OF USE

(75) Inventors: Valerian V. Plotnikov, Sunderland, MA (US); Andrzej Rochalski, South Hadley, MA (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 152 days.

(21) Appl. No.: 12/740,380

(22) PCT Filed: Oct. 31, 2008

(86) PCT No.: PCT/US2008/081961
§ 371 (c)(1),
(2), (4) Date: Apr. 29, 2010

(87) PCT Pub. No.: WO2009/059110
PCT Pub. Date: May 7, 2009

(65) Prior Publication Data
US 2010/0238968 A1    Sep. 23, 2010

Related U.S. Application Data

(60) Provisional application No. 60/984,432, filed on Nov. 1, 2007.

(51) Int. Cl.
*G01K 17/00* (2006.01)
(52) U.S. Cl.
USPC .......................................... 374/33

(58) Field of Classification Search
USPC ........................................... 374/33
See application file for complete search history.

(56) References Cited

U.S. PATENT DOCUMENTS

| | | | | |
|---|---|---|---|---|
| 4,259,843 A | * | 4/1981 | Kausch | 62/3.1 |
| 4,643,879 A | * | 2/1987 | Hanaway | 422/566 |
| 4,681,741 A | * | 7/1987 | Hanaway | 422/509 |
| 5,000,921 A | * | 3/1991 | Hanaway et al. | 422/520 |
| 5,096,670 A | * | 3/1992 | Harris et al. | 422/65 |

(Continued)

FOREIGN PATENT DOCUMENTS

| EP | 266155 A2 * | 5/1988 |
|---|---|---|
| WO | WO81/01045 | 4/1981 |

(Continued)

OTHER PUBLICATIONS

Cooper, A., et al., "Isothermal Titration Microcalorimetry", Chapter 11, Methods in Molecular Biology, vol. 22, Optical Spectroscopy and Macroscopic Techniques, edited by C. Jones, et al.*

(Continued)

*Primary Examiner* — Lisa Caputo
*Assistant Examiner* — Jamel Williams (57) ABSTRACT

An automatic pipette assembly for an isothermal titration micro calorimetry system, comprising a pipette housing, a syringe with a titration needle arranged to be inserted into a sample cell for supplying titrant, and a linear activator for driving a plunger in the syringe, the titration needle is rotatable with respect to the housing and is provided with a stirring paddle arranged to stir fluid in the sample cell, wherein the automatic pipette assembly comprises a stirring motor for driving the rotation of the titration needle. There is also provided an isothermal titration micro calorimetry system.

13 Claims, 8 Drawing Sheets

U.S. PATENT DOCUMENTS

| | | | |
|---|---|---|---|
| 5,813,763 A * | 9/1998 | Plotnikov et al. | 374/11 |
| 6,395,231 B1 * | 5/2002 | Kraemer et al. | 422/510 |
| 6,573,088 B2 * | 6/2003 | Gemmell et al. | 435/286.4 |
| 2003/0032171 A1 * | 2/2003 | Gemmell et al. | 435/286.2 |

FOREIGN PATENT DOCUMENTS

| | | | |
|---|---|---|---|
| WO | WO 8101045 A * | 4/1981 | |
| WO | WO87/00086 | 1/1987 | |
| WO | WO 8700086 A * | 1/1987 | |

OTHER PUBLICATIONS

Cooper, A., et al., "Isothermal Titration Microcalorimetry", Chapter 11, Methods in Molecular Biology, vol. 22, Optical Spectroscopy and Macroscopic Techniques, edited by C. Jones, et al. (1994).*

Doyle, M., Titration Microcalorimetry, Current Protocols in Protein Science, Supplement 18 (1999) 20.4.1-20.4.24.*

Cooper, A., et al., "Isothermal Titration Microcalorimetry", Chapter 11, Methods in Molecular Biology, vol. 22, Optical Spectroscopy and Macroscopic Techniques, edited by C. Jones, et al., 1994.

* cited by examiner

ISOTHERMAL TITRATION MICROCALORIMETER APPARATUS AND METHOD OF USE

CROSS-REFERENCE TO RELATED APPLICATIONS

This application is a filing under 35 U.S.C. §371 and claims priority to international patent application number PCT/US2008/081961 filed Oct. 31, 2008, published May 7, 2009 as WO2009/059110, which claims priority to U.S. provisional patent application No. 60/984,432 filed Nov. 1, 2007; the disclosure of which is incorporated herein by reference in its entirety.

BACKGROUND OF THE INVENTION

1. Field of the Invention

The present invention relates generally to microcalorimeters and more specifically to features that improve the performance of microcalorimeters, especially isothermal titration calorimeters.

2. Background

Microcalorimeters are broadly utilized in fields of biochemistry, pharmacology, cell biology, and others. Calorimetry provides a direct method for measuring changes in thermodynamic properties of biological macromolecules. Microcalorimeters are typically two cell instruments in which properties of a dilute solution of test substance in an aqueous buffer in a sample cell are continuously compared to an equal quantity of aqueous buffer in a reference cell. Measured differences between the properties of the two cells, such as temperature or heat flow, are attributed to the presence of the test substance in the sample cell.

One type of microcalorimeter is an isothermal titration calorimeter. The isothermal titration calorimeter (ITC) is a differential device, but operates at a fixed temperature and pressure while the liquid in the sample cell is continuously stirred. The most popular application for titration calorimetry is in the characterization of the thermodynamics of molecular interactions. In this application, a dilute solution of a test substance (e.g., a protein) is placed in the sample cell and, at various times, small volumes of a second dilute solution containing a ligand, which binds to the test substance, are injected into the sample cell. The instrument measures the heat which is evolved or absorbed as a result of the binding of the newly-introduced ligand to the test substance. From results of multiple-injection experiments, properties, such as, the Gibbs energy, the association constant, the enthalpy and entropy changes, and the stoichiometry of binding, may be determined for a particular pairing between the test substance and the ligand.

While currently utilized ITCs provide reliable binding data results, their widespread utilization in the early stages of drug development have been limited by several factors: the relatively high amounts of protein required to perform a binding determination (e.g., about 0.1 milligram (mg) to about 1.0 mg of a protein), the time required to perform the measurement, and the complexity of using conventional ITCs. Due to the extremely high costs of biological substances used in research, there is a need to reduce the amount of biological substance used for each experiment. A reduction in the amount of the biological substance used in a calorimeter experiment, will require a more accurate, sensitive, and reliable titration calorimeter than what is currently available.

Furthermore, gathering binding data utilizing prior art ITCs require extensive preparation and skill by the practitioner. For example, using prior art ITCs, the reference and sample cells are first filled respectively with the reference substance and sample substance via a corresponding cell stem. Next, a syringe of the ITC is filled with a titrant. Then a needle of the ITC is placed in the sample cell via a cell stem leading to the sample cell while the syringe fits into a holder on the ITC enabling the syringe to rotate around its axis. Subsequently, the syringe is aligned with the sample cell so that the needle does not touch either the cell stem or the sample cell. Then, the syringe is connected to a stirring motor and a linear activator of the ITC, wherein the stirring motor and the linear activator must also be aligned with the sample cell.

As would be appreciated by a reading of the above-described prior art procedure, utilizing prior art ITCs, the quality of binding measurements performed with these prior art ITCs depends heavily of the operator's skills and experience, and involves a considerable amount of preparation time.

Figure 1:
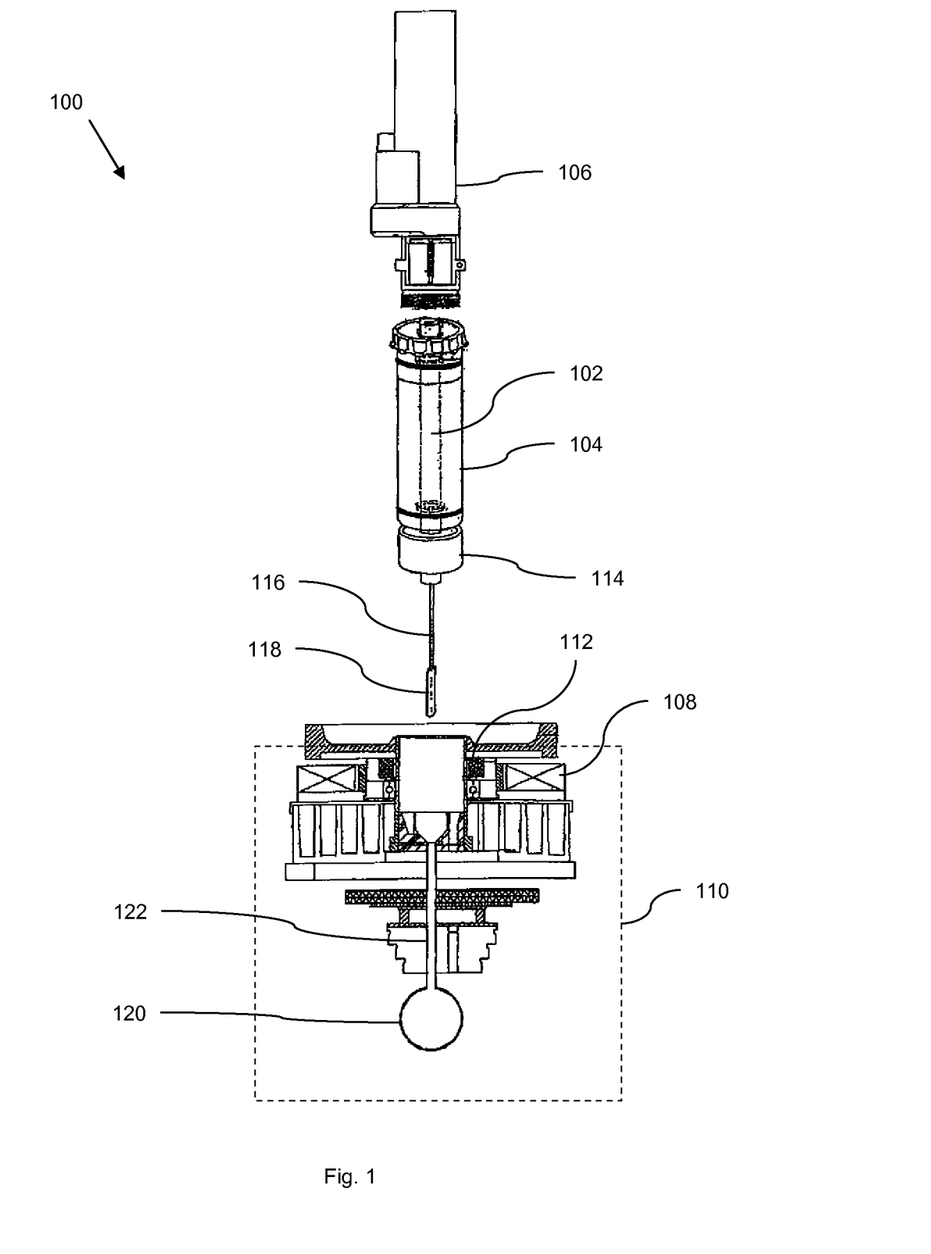
FIG. 1 shows a schematic example of a prior art isothermal titration microcalorimeter highlighting the automatic pipette feature of the microcalorimeter.

More recently developed prior art ITCs have attempted to simplify the preparatory procedures described above. For example, in one such prior art ITC, which is partly shown in FIG. 1 as ITC 100, a syringe 102, a syringe holder 104, and a linear actuator 106, which actuates syringe 102's plunger, are integrated into a single unit referred to as an automatic pipette. ITC 100 further comprises a stirring mechanism comprising a stirring motor 108, which is attached to calorimeter body 110. ITC 100 also comprises an inner magnet couple 112 located around syringe 102, and an outer magnet couple 114 located on calorimeter body 110 in close proximity to stirring motor 108. The rotation from stirring motor 108 to syringe 102 is transferred via magnet couplings 112 and 114. Attached to syringe 102 is a needle 116 and a paddle 118. The needle 116 is arranged to be inserted into a sample cell 120 via a cell stem 122 for performing ITC experiments. For reference purposes, ITC 100, also comprises a reference cell, not shown, in communication with the ambient atmosphere via a reference cell stem.

The prior art design discussed above and depicted in FIG. 1 has certain limitations. For example, since the magnet coupling is a soft/flexible transmission, it is prone to resonant vibration of the stirrer at certain rotation speeds and accelerations, which negatively affects the instrument's sensitivity. The resonant vibration can be reduced by either employing a less sensitive feedback mechanism controlling the rotation speed (which leads to less stable rotation speed), or by lowering the rotation speed. However, less stable rotation speed also reduces the ITC's sensitivity, while lower rotation speed impedes proper mixing of reagents which reduces the ITC's accuracy.

Another limitation of the prior art design is that the stirring motor and the magnet coupling are placed closely to the sensitive measuring unit of the instrument and generates a substantial alternating magnetic field that produces electric noise which negatively affects the operation of the ITC's sensitive electronic circuitry. Since the ITC's sensors process signals of approximately $10^{-9}$ volts, and the noise generated by the motor and the magnetic coupling is a reciprocal of the distance between the sensor and the source of the noise, further improvements in the performance characteristics of this ITC design become increasingly challenging. As stated earlier, one of the underlying factors affecting the design of new microcalorimeters is the need to reduce the amount of biological substance used for each experiment. This requires smaller sample cells and shorter cell stems which in turn leads to, smaller distances between the cell sensor and the motor and magnetic coupling (source of electric noise), which limits the instrument's sensitivity.

The invention described herein is aimed to improve the aforementioned characteristics and use of prior art ITCs such that the sensitivity of the ITC is improved, the amount of biological substance necessary for testing is reduced, the reliability of the results generated by the ITC is improved, and use of the ITC is eased.

SUMMARY OF THE INVENTION

The object of the invention is to provide a new automatic pipette assembly for an isothermal titration micro calorimetry system and an ITC system, which pipette assembly and ITC system overcomes one or more drawbacks of the prior art. This is achieved by the pipette assembly and the ITC system as defined in the independent claims.

One advantage with the present pipette assembly and the associated ITC system is that it makes it possible to reduce the cell compartment volume by about a factor of seven as compared to prior art ITCs, without a reduction in sensitivity, and with a significantly faster response time. Such an ITC system permits the performance of experiments with about 10 times less protein sample, and with only a total of about 2 to about 4 titrations per hour.

In addition to reducing the costs associated with running the ITC experiment, a smaller cell volume also extends the number of ITC applications. For example, the range of binding affinities that can be measured by ITC is dictated by a parameter called "c value," which is equal to the product of the binding affinity ($K_a$) and the total concentration ($M_{total}$) of macromolecule ($c=[M_{total}]K_a$). For accurate affinity determination, the c value must be between 1 and 1,000. A decrease in the cell volume by a factor of ten results in a similar increase in c value if the same amount of protein is used, and, consequently, the ability to measure weak binders. This ability is especially important in the early stages of drug discovery, in which binding affinities are weak, especially in conjunction with a fully automated instrument.

DETAILED DESCRIPTION OF THE INVENTION

Figure 2:
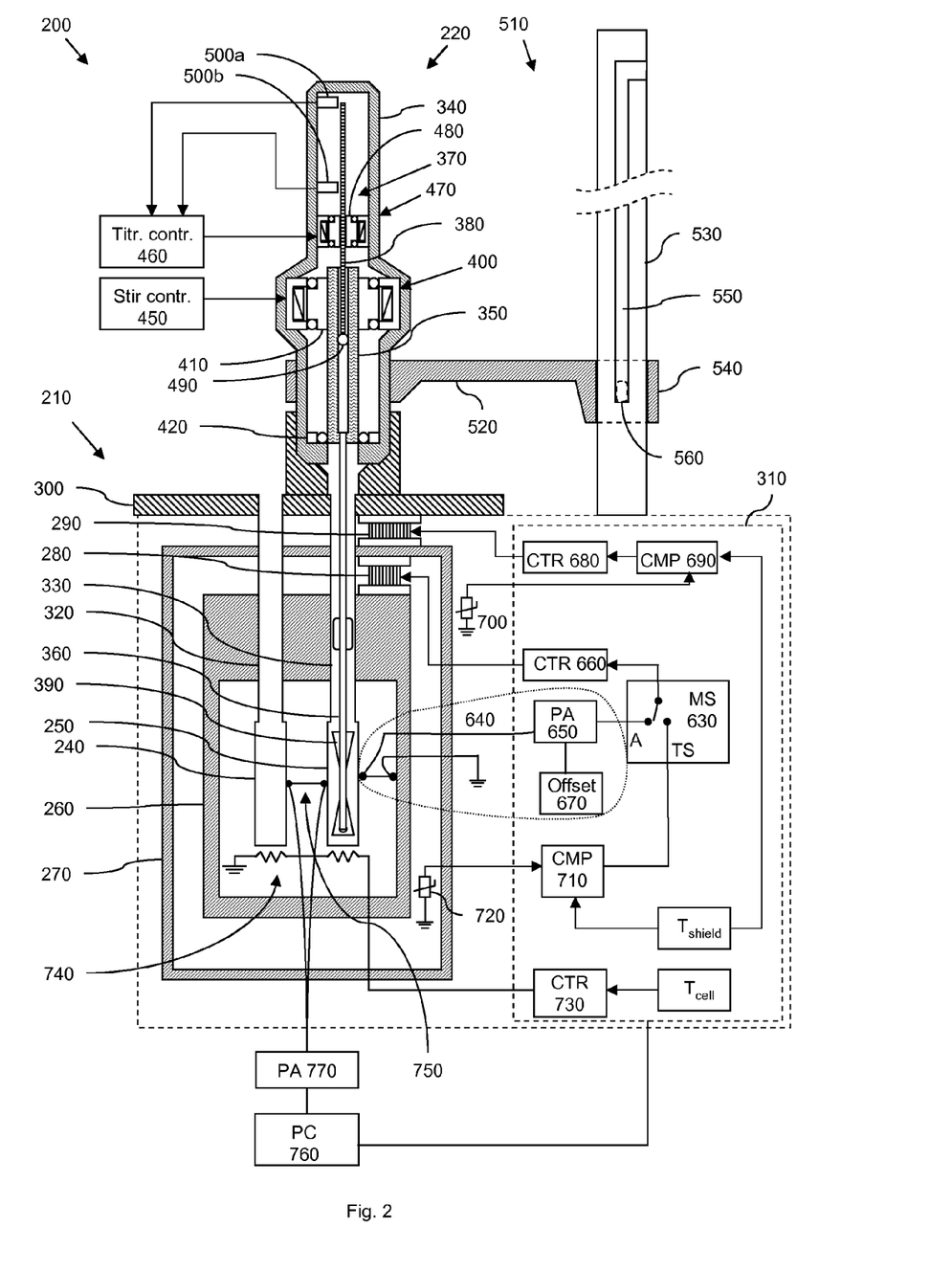
FIG. 2 shows, in cross-section, a schematic embodiment of an isothermal titration calorimeter system of the present invention with a guiding mechanism.

FIG. 2 schematically shows one embodiment of an ITC system 200 according to the present invention. The ITC system 200 comprises a micro calorimeter 210 and an automatic pipette assembly 220. The micro calorimeter 210 comprises a reference cell 240 and a sample cell 250 which are designed to be essentially identical in heat capacity and volume. The cells 240 and 250 are comprised of a suitable chemically inert and heat conductive material, such as gold, Platinum, tantalum, hastelloy or the like. The cells 240 and 250 may be of essentially any suitable shape, but it is desirable that they are of the same shape, that they are possible to arrange in a fully symmetric arrangement, and that efficient mixing of the titrant with the sample may be achieved. In the disclosed embodiment, the cross-section of the cells 240 and 250 is rectangular, and the cross-section in the transverse horizontal direction may be circular, resulting in coin shaped cells with circular facing surfaces.

In order to reduce any external thermal influences to a minimum, the, reference cell 240 and the sample cell 250 are both enclosed by a first thermal shield 260 which in turn is enclosed by a second thermal shield 270. The thermal shields 260, 270 may be comprised of any suitable thermally conductive material such as silver, aluminum, cupper or the like. The shields 260, 270 may further be comprised of one or more thermally interconnected sub shields (not shown, to provide even further stable temperature conditions for the calorimetric cells 240, 250.

In order to control the temperature of the shields 260, 270, thermal control means may be arranged to control the temperature thereof. In an ITC system said thermal control means are mainly used to set the "isothermal" temperature of the calorimeter, ie. of the thermal shields 260, 270, before the titration experiments are initiated. But as will be disclosed in greater detail below, said thermal control means may also be used to improve the adiabatic behavior of the calorimeter. According to one embodiment, the thermal control means are comprised of one or more heat pump unit, such as a thermoelectric heat pump device based on the peltier effect or the like. Other types of thermal control means include thermostatically controlled liquid baths, mechanical heat pumps, chemical heating or cooling systems or the like.

In the disclosed embodiment a first heat pump unit 280 is arranged to transfer heat energy between the first 260 and second thermal shields 270, a second heat pump unit 290 is arranged to transfer heat energy between the second thermal shield 270 and a heat sink 300 in thermal contact with the ambient temperature. A temperature controller 310 is arranged to control the first and second heat pump units 280, 290 so that the desired temperature conditions are achieved. The temperature controller 310 and associated sensors will be disclosed in more detail below.

A reference cell stem 320 and a sample cell stem 330 provides access to the reference cell 240 and sample cell 250, respectively, for supplying reference and sample fluids, titration fluid, washing of the cells etc. In the disclosed embodiment, the cell stems 320 and 330 both extends essentially vertically through both thermal shields and the heat sink to provide direct communication with cells 240 and 250 and the cell stems 320 and 330 each support their respective cell 240 and 250 in the cavity of the first thermal shield 260.

The automatic pipette assembly 210 comprises a pipette housing 340, a syringe 350 with a titration needle 360 arranged to be inserted into the sample cell 250 for supplying titrant, and a linear activator 370 for driving a plunger 380 in the syringe 350. The titration needle 360 is rotatable with respect to the housing 340 and is provided with a stirring paddle 390 arranged to stir sample fluid in the sample cell 250 in order to achieve efficient mixing of titrant and sample fluid. The automatic pipette assembly 210 further comprises a stirring motor 400 for driving the rotation of the titration needle 360.

In the embodiment disclosed in FIG. 2 the stiffing motor 400 is a direct drive motor with a hollow rotor 410 arranged concentric with the syringe 350 and the titration needle 360. The syringe 350 is at its upper end supported for rotation by the stiffing motor 400 and at the lower end by a bearing 420. Both the stirring motor 400 and the bearing 420 are schematically disclosed as comprising ball bearings, but any other type of bearing, bushings or the like capable of providing smooth and low friction rotation of the titration needle 360 may be used.

Figure 3:
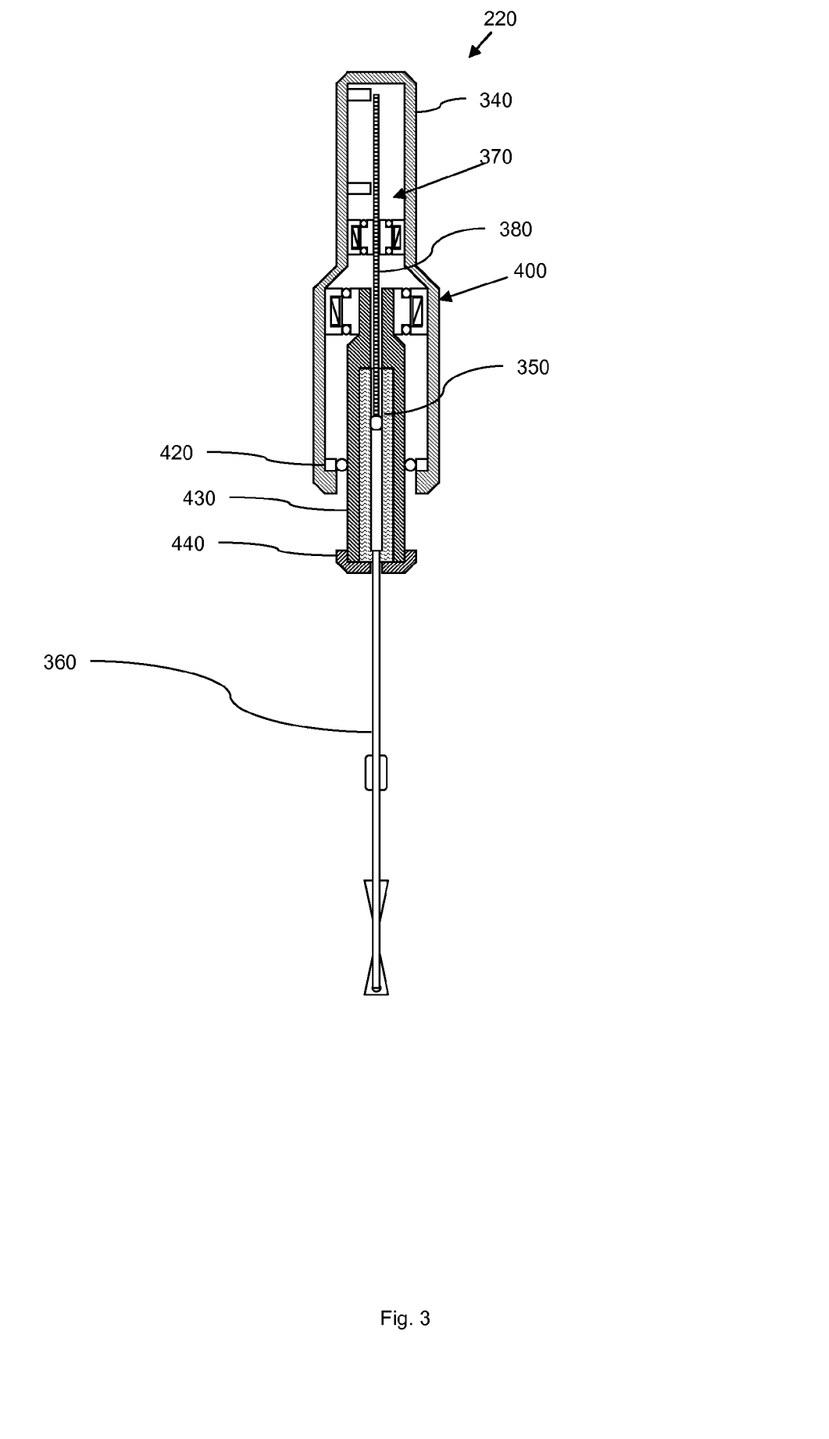
FIG. 3 shows, in cross-section, a schematic embodiment of an automatic pipette assembly for an isothermal titration micro calorimetry system.

In the embodiment disclosed in FIG. 2, the syringe 350 is arranged to be rotatable with respect to the housing 340 and the titration needle 360 is non-rotatably attached to the syringe 350. In an alternative embodiment (not shown in figs.), the needle 360 is rotatable with respect to the syringe 350 and the syringe 350 static with respect to the pipette housing 340. FIG. 3 shows an alternative embodiment, wherein the syringe 350 is detachably arranged in a rotation frame 430 within the pipette housing 340, the rotation frame 430 being rotably supported by the motor 400 and bearing 420. In the disclosed embodiment, the syringe 350 is retained in the rotation frame 430 by a cap 440 that is detachably attached to the rotation frame 430 by threads or the like. By removing the cap 440, the syringe 350 with the titration needle 360 can be replaced.

In an alternative embodiment, not shown in the figures, the stirring motor 400 drives the titration needle for rotation by a rotation transmission arrangement, such as a drive belt arrangement, a drive wheel arrangement or the like. In such an arrangement, the drive motor may be placed at an ever greater distance from the calorimetric cells.

The stirring motor is controlled by a stir controller 450 of the ITC system. The stir controller be a conventional BLDC. The linear actuator is controlled by a titration controller 460 of the ITC system. The stir and titration controllers 450, 460 may be arranged in the pipette assembly 220, and in turn connected to the ITC control system (not shown in detail), or they may be an integrated part of the ITC control system.

In the disclosed embodiment, the linear activator 370 comprises a stepper motor 470 arranged to drive a threaded plunger 380 that extends coaxially through the hole of a hollow rotor 480 and into the syringe 350 wherein it is rotatably attached to a pipette tip 490 that seals against the inner wall of the syringe 350 to allow displacing a precise volume of titration liquid from syringe 350. The pipette assembly further comprises position sensors 500a, 500b for detecting two predetermined positions of the threaded plunger 380. The linear activator 370 may be of any other type capable of perform controlled linear motion with sufficient precision. This design allows syringe to be rotated independently of the main body 340 of the pipette assembly 220; at the same time, the linear activator 370 can drive the threaded plunger 380.

In the ITC system the titration 460 controller is arranged to control the linear activator of the pipette assembly 220. According to one embodiment, titration controller 460 uses the position sensors 500a, 500b for detecting two predetermined positions of the threaded plunger, and the titration controller 460 is arranged to register the two predetermined positions of the threaded plunger 380 and to determine the pitch of the threads of the plunger 380 from the number of steps performed by the stepper motor 470 to move the threaded plunger 380 between said positions. The so determined pitch of the threaded plunger is thereafter used by the pipette controller to increase the accuracy of the titration pipette, when displacing small volumes of titrant.

In the disclosed embodiments, the pipette assembly housing 340 serves as mounting base for the stators of the stirring motor 400 and the linear activator 470. The housing 340 may further comprise an attachment section for precise positioning of the pipette assembly with respect to the sample cell stem.

The automatic pipette assembly 220 with an integrated stiffing motor 400 arranged at the upper end of, or above the syringe 350 not only increases the distance between the stirring motor 400 (i.e., the source of an alternating electromagnetic field) and the sensitive electronic circuitry, which is located at and/or nearby the thermal core of the calorimeter, but it also allows for the reduction in the amount of power needed to operate the stirring motor 400. That is, due to the placement of the stiffing motor 400 on the pipette assembly 220, the size of the stirring motor 400 is not determined by the space between the sample cell and the reference cell as it is determined by prior art ITCs that place the stiffing motor on the calorimeter housing (FIG. 2). In the prior art, then, the cell stems protrude through the center of rotation of the magnetically coupled stirrer. Therefore, the lower limit of size for the stirrer mechanism is determined by the spacing between the cell stems. Accordingly, the size of the stiffing motor of the present invention can be significantly reduced, e.g., by a factor of about 5 times that of stiffing motors found in prior art ITCs, thereby resulting in a significant reduction in the amount of power needed to operate the ITC, e.g., about 2 watts versus the 100 watts used to power conventionally known ITCs.

The reduction in size of the stirring motor to a size of about five times less than stirring motors of prior art ITCs, and the placement of the stirring motor on the pipette such that the stirring motor is at a distance of about 50 millimeters or more away from the sensitive electronic circuitry of the calorimeter, and the removal of the magnetic coupling, closes the magnetic field that exists in conventionally used ITCs. Accordingly, the sensitivity of the inventive ITC is raised by the lower power, the lower heat, the lower electricity, and the lower noise and vibration caused by the placement of the stirring motor as disclosed herein. Furthermore, the disclosed embodiments also exclude magnetic coupling which is an additional source of alternating electro-magnetic field.

These improvements reduce the electrical noise induced in the sensitive electronic circuitry which, in turn, helps improve the calorimeter's sensitivity, whereby the volume of the sample and reference cells may be significantly reduced. Reducing the size of the sample cell and its corresponding cell stem, in turn, reduces the amount of biological substance used for each experiment.

The following Table 1 represents certain key dimensions of the cell stems and test and reference cells of both the prior art ITC and the ITC of the present invention. As shown in Table 1, the inventive ITC, which places the stirring motor directly on the pipette subassembly, rather than positioning it on the calorimeter body, allows a smaller volume of test substance to be used, thereby reducing the costs associated with conducting calorimeter experiments.

TABLE 1

|  | Prior Art ITC | Inventive ITC |
|---|---|---|
| Stem Interior Diameter | 2.6 millimeters | 2.0 millimeters |
| Cell stem Length | 72.0 millimeters | 40.5 millimeters |
| Cell stem Volume | 382.0 microliters | 127.0 microliters |
| Cell Interior Diameter | 22.0 millimeters | 11.0 millimeters |
| Cell Thickness | 3.7 millimeters | 2.2 millimeters |
| Cell Volume | 1,400 microliters | 200 microliters |

Figure 4:
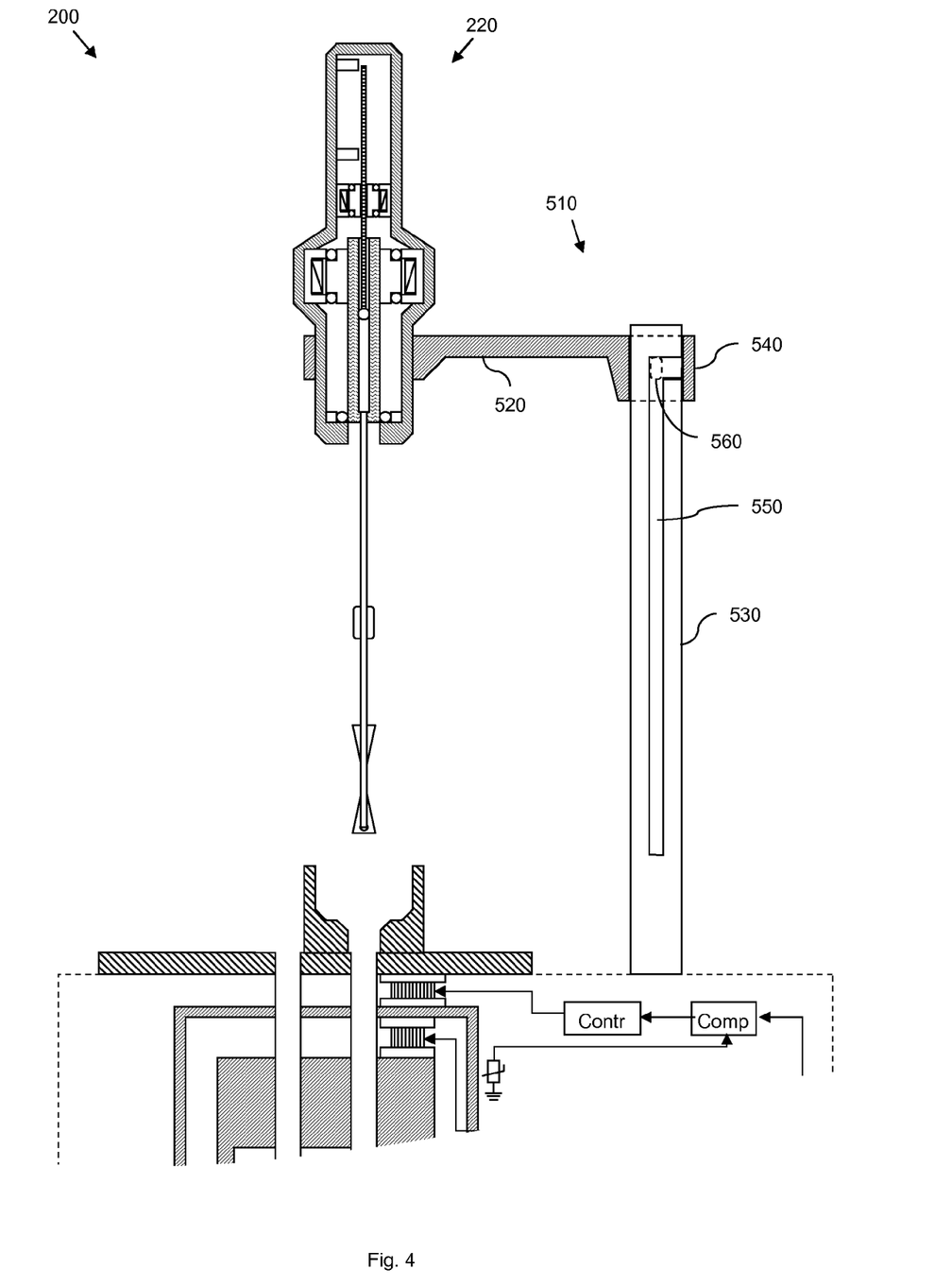
FIG. 4 shows a section of the ITC system shown in FIG. 2, wherein the pipette assembly is retracted from the sample cell.

According to one embodiment, the micro titration calorimetry system 200 is provided with a pipette guiding mechanism 510 arranged to guide the pipette assembly 220 between and into at least two positions of operation. The first position of operation is a pipette washing position 580 wherein the titration needle 360 is inserted in a washing apparatus (see FIGS. 5a-5c), and the second position of operation is a titration position 560 wherein the syringe is inserted into the sample cell 250 for calorimetric measurements. In the embodiment of FIG. 2, the guiding mechanism 510 is comprised of a pipette arm 520 that supports the pipette assembly 220, and an essentially vertical guide rod 530. The pipette arm 520 is moveably attached by a sleeve 540 to the guide rod 530, but its motion about the guide rod is restricted by a guide groove 550 in the guide rod 530 and a guide pin 560 that protrudes from the inner surface of the sleeve 540 and which fits into the guide groove 550. The disclosed guiding mechanism 510 is of rotational type, and the positions of operation are arranged at equal distance about the centre of rotation of the guide assembly but at different angular positions, wherein movement of the pipette assembly 220 in the vertical direction is restricted to the angular positions of the positions of operation, and wherein rotational movement of the pipette assembly 220 between the angular positions only is permitted when the titration needle 260 is fully retracted from respective positions of operation. FIG. 4 shows the guide mechanism 510 in a position wherein the pipette assembly 220 is fully retracted from the titration position, i.e. from the sample cell 250. At this position the guiding mechanism 510 restricts the possible movement of the pipette arm 520 to a vertical movement down into the titration position, or a rotational movement to reach another position of operation. In a micro titration calorimetry system 200 with two positions of operation, the washing apparatus 600 may be arranged to allow filling of titrant to the pipette assembly 220 after washing of the pipette assembly is completed. Alternatively, filling of the pipette may be performed through other means, such as a specific filling port in the syringe or the like.

Figure 5A:
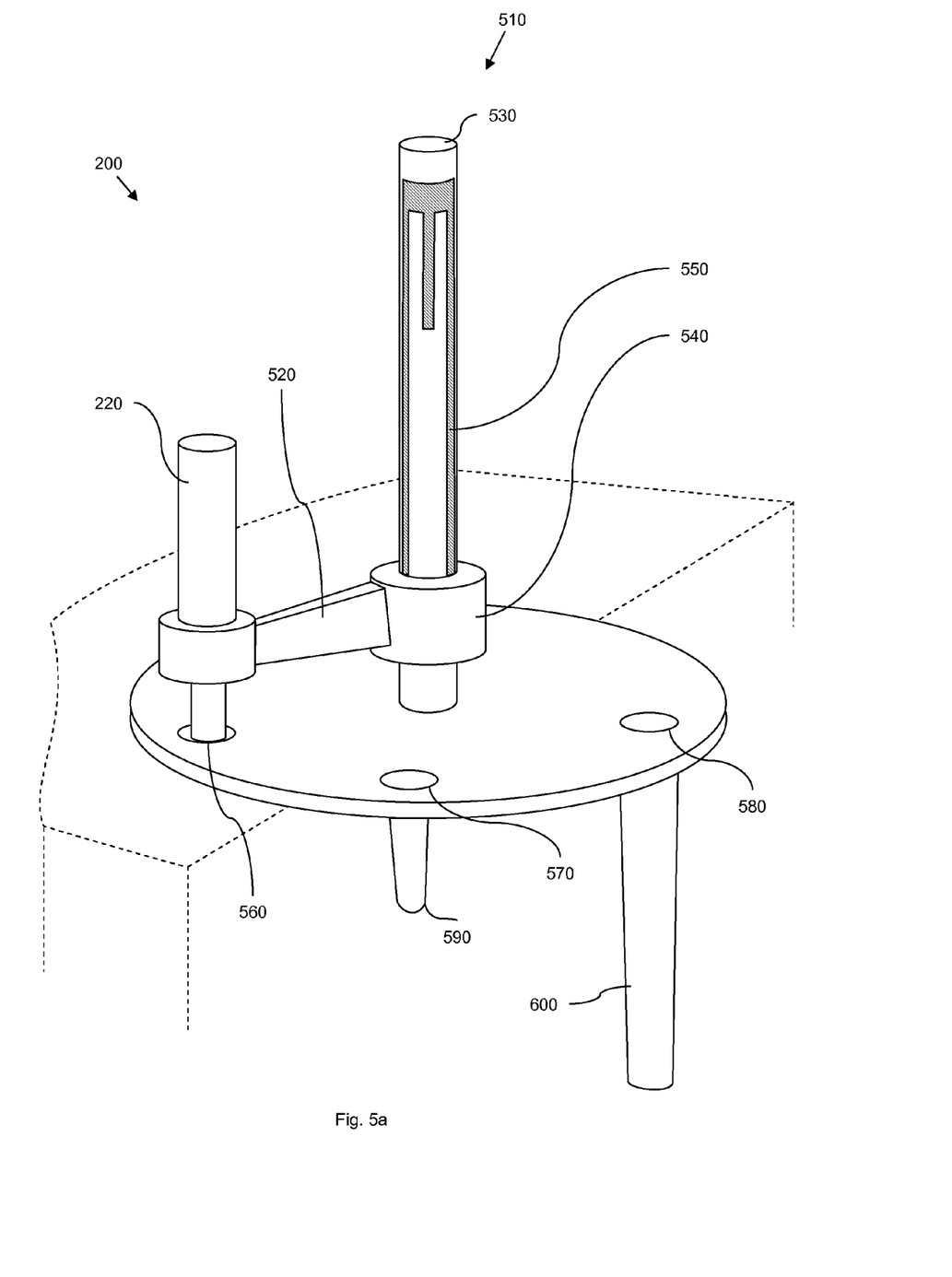
FIGS. 5a to 5c show a schematic embodiment of a guiding mechanism for an isothermal titration calorimeter system in perspective.
Figure 5B:
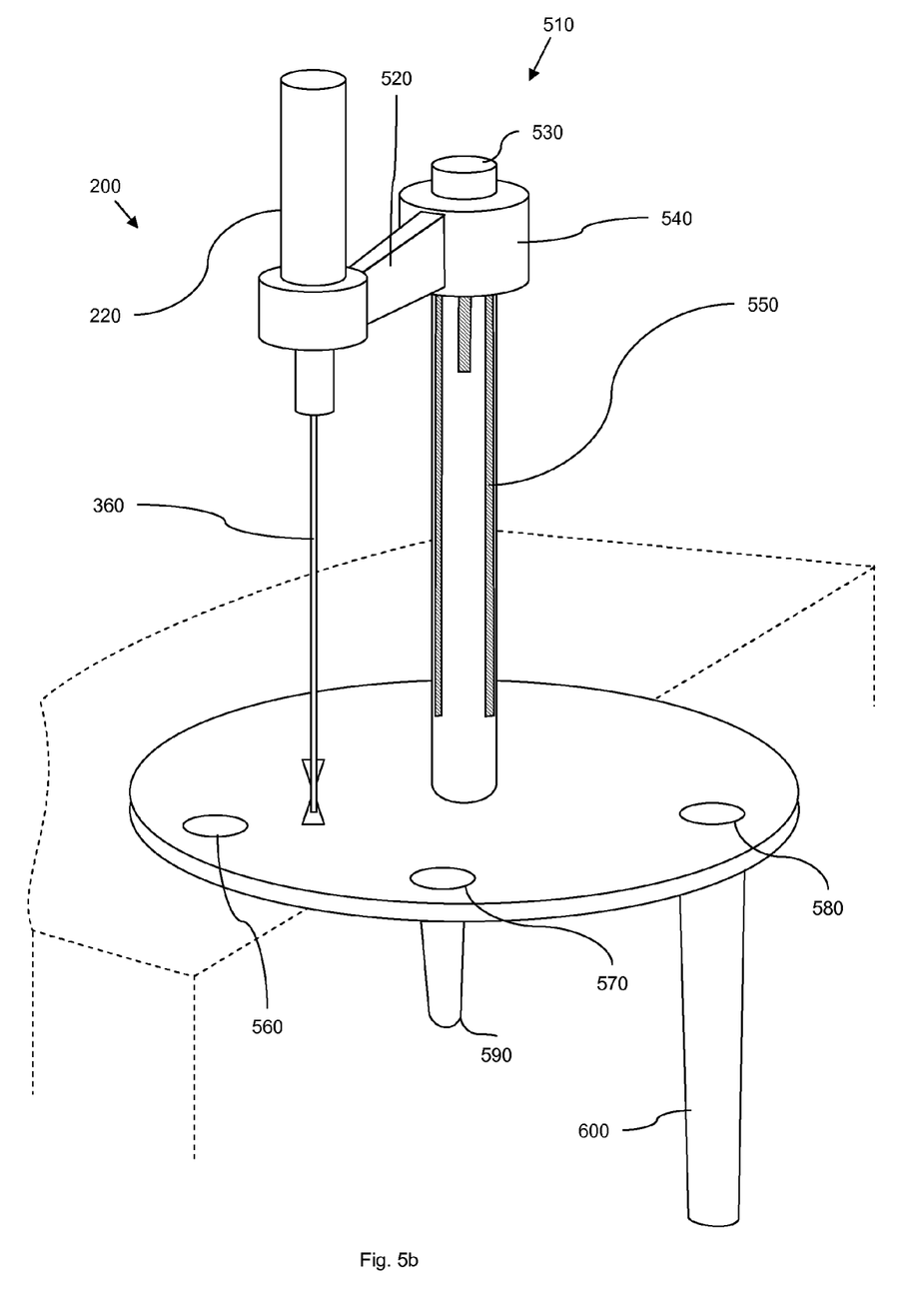
Figure 5C:
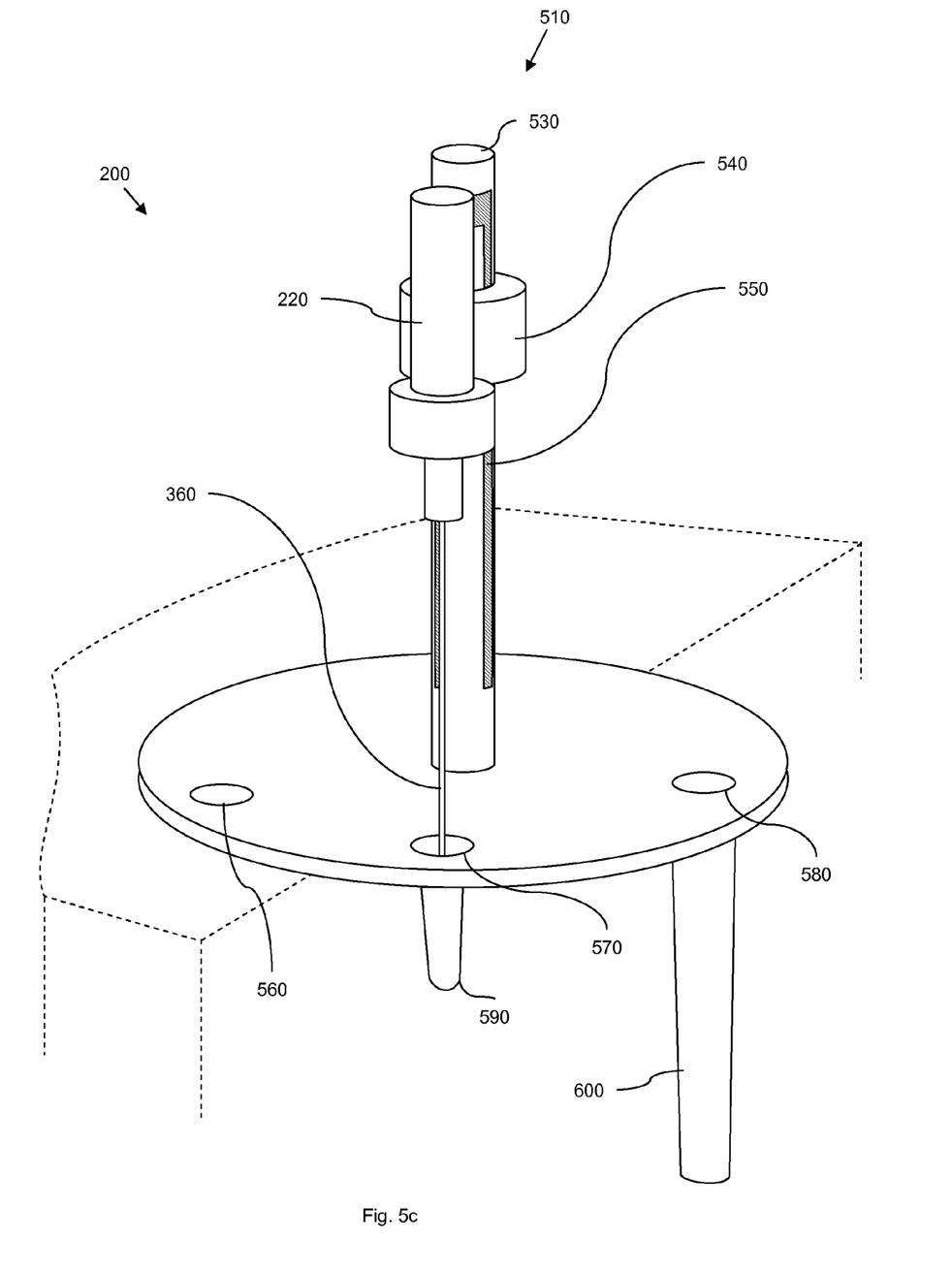

FIGS. 5a to 5c show a schematic perspective view of one embodiment of a micro titration calorimetry system 200 with a pipette guiding mechanism 510, arranged to guide the pipette assembly 220 to and from three different positions of operation 560, 570, 580. According to one embodiment, the third position of operation is a titrant filling position 570, wherein the titration needle 360 is inserted in a titrant source 590. FIG. 5a shows the guiding mechanism 510 in a state wherein the pipette assembly 220 is in the titration position 560. FIG. 5b shows the guiding mechanism 510 in a state intermediate the titration position 560 and the filling position 570. FIG. 5c shows the guiding mechanism 510 in a state wherein the titration needle 360 of the pipette assembly 220 is in the filling position 570. As is disclosed in FIGS. 4a to 5c, the vertical guide grooves 550 associated with a specific position of operation 560, 570, 580 may be arranged to position the pipette assembly 220 at a predetermined height with respect to the operation to be performed.

Figure 6:
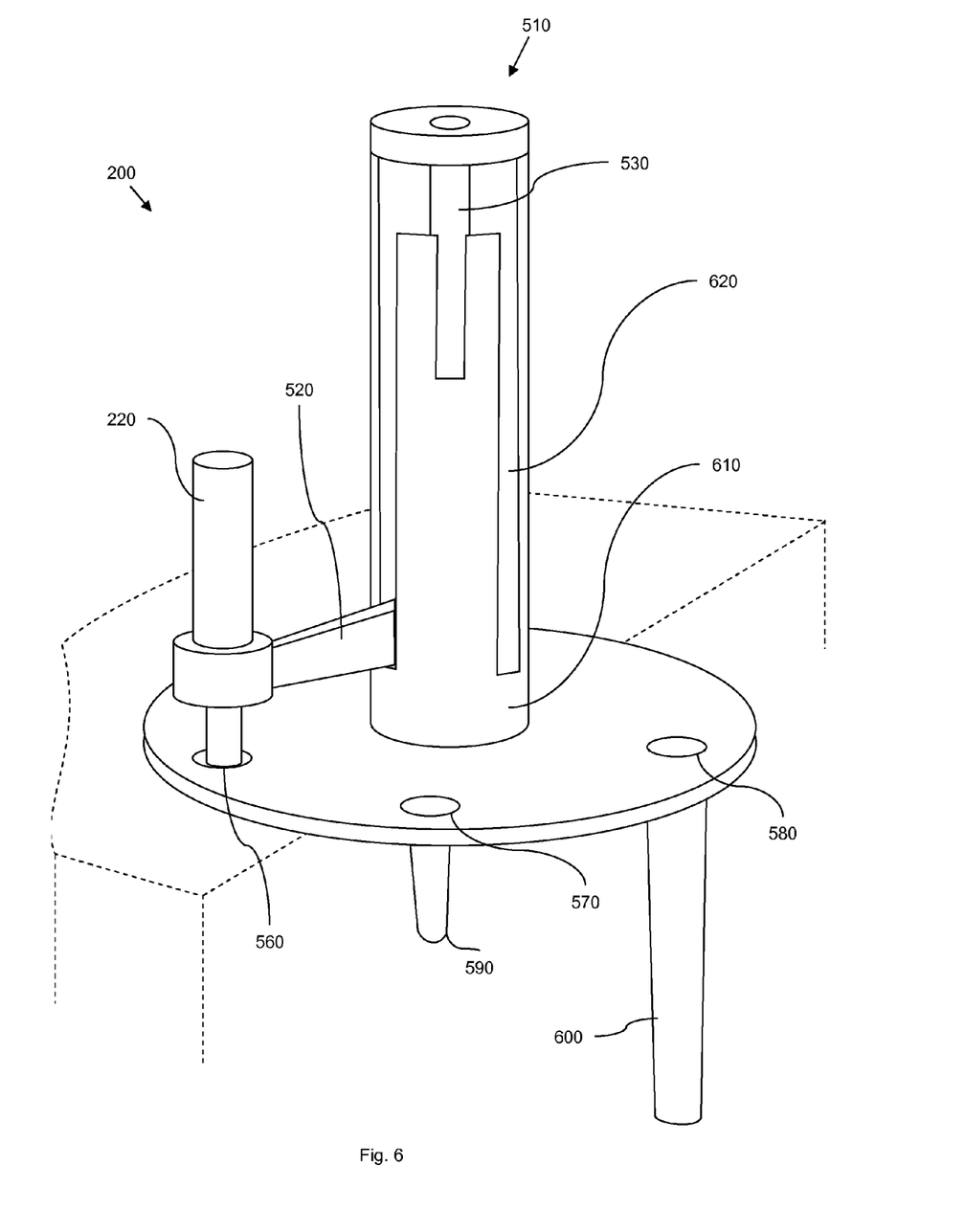
FIG. 6 shows another schematic embodiment of a guiding mechanism for an isothermal titration calorimeter system in perspective.

FIG. 6 shows another embodiment of the guide mechanism 510, wherein the guide groove in the guide rod 530 is replaced by a coaxial external guide sleeve 610 with corresponding guide paths 620 for the guide arm 520.

According to one embodiment, the micro titration calorimetry system 200 comprises one or more position sensors, not shown, arranged to register when the pipette assembly 220 is positioned at one or more of the positions of operation 560, 570, 580, and wherein the associated operation is restricted by the state of the position sensor. A sensor may, e.g. be arranged to register when the pipette assembly 220 is in correct position for titration 560, and the calorimetry system 200 may be arranged to prevent start of a titration operation unless said sensor confirms that the pipette assembly 220 is in correct position.

Again referring to the figures, the guiding mechanism 510 ensures proper alignment and positioning of pipette assembly 220 in the sample cell 250 etc. All elements of the pipette assembly 220 (syringe, needle, paddle, plunger, linear activator, hollow rotor) and the guiding mechanism 510 are preferably precisely aligned during the manufacturing process and do not require any additional alignment during the use of the instrument. The pre-set factory alignment significantly improves usability and reliability of the instrument, considerably reduces the amount of preparatory time for an experiment, and makes the quality of measurements independent of the user skills. The guiding mechanism 510 also enables proper positioning of the pipette assembly 220 in the washing apparatus 600 for cleaning and drying of the syringe and e.g. for filling the syringe with titrant.

An exemplary method for utilizing the ITC apparatus disclosed herein comprises the non-manual alignment, both in depth and in breadth, of the syringe for filling titrant, washing the pipette, and delivering the titrant to the syringe.

An exemplary method for operating the inventive ITC apparatus comprises using the guiding mechanism 510 to position the pipette for filling the syringe with titrant (see FIG. 5c). In this position, the end of the needle with the paddle is placed in the titrant. The plunger of the syringe is moved from its lower position to its upper position thereby filling the syringe with the titrant. The sample cell is filled with the sample solution via the cell stem using an auxiliary syringe. Using the guiding mechanism, the pipette is moved to a position for performing an experiment (see FIG. 5a). The program for performing the experiment is activated. Consistent with the program used for the experiment, the rotor of the stirring motor rotates the syringe, needle, and paddle with the assigned speed enabling proper mixing of the reagents. Consistent with the program used for the experiment (e.g., when a certain temperature and/or equilibrium are reached), the linear activator moves the plunger and injects the titrant into the sample solution. The injection can be done discretely (step-by-step) or continuously, depending on the program settings. The calorimeter continuously measures and records the heat release/absorption versus time associated with the interaction of reagents. The analysis of the results is done according to the established algorithm.

Referring again to FIG. 2, the temperature controller 310 is arranged to control the first and second heat pump units 280, 290 in accordance with predetermined control-modes. The temperature controller 310 is schematically disclosed by functional blocks, and it may either be designed as an electronic circuit, as a software in a CPU based controller, or as a combination thereof. In the disclosed embodiment, the thermal controller 310 may be switched between two modes of operation:

Isothermal mode
Thermal set mode
by means of a mode select block 630.

In the isothermal mode the thermal controller 310 is arranged to control the first heat pump 280 to minimize the temperature difference between the sample cell 250 and the first thermal shield 260. The temperature difference between the sample cell 250 and the first thermal shield 260 is registered by a temperature sensor arrangement 640 in communication with the temperature controller 310. In the disclosed embodiment, the temperature sensor arrangement 640 is a differential thermocouple that gives a non-zero signal when there is a temperature difference between the two points of registration, and the output from the thermocouple is connected to a preamplifier block 650 in the temperature controller 310. The out-put from the preamplifier 650 is directed by the mode select block 630 to a first heat pump controller block 660 that controls the first heat pump 280 in response to the signal from the preamplifier 650. By this arrangement, the first heat pump controller 660 will strive to compensate for any thermal difference between the sample cell 250 and the first thermal shield 260, whereby a compensated adiabatic state is achieved in the calorimeter 210. In order to compensate for minor systematic drifts in adiabatic behavior, an offset parameter 670 may be applied on the signal from the preamplifier 650. The offset parameter 670 may be set during calibration of the calorimeter 210. In the isothermal mode, the temperature controller 310 is arranged to control the second heat pump 290 to keep the second thermal shield 270 at a predetermined temperature, as is defined by a parameter $T_{shield}$. The control of the second heat pump 290 is performed by a second heat pump controller block 680 that receives an output from a second comparator block 690 wherein $T_{shield}$ is compared with the present temperature of the second shield registered by a second shield thermal sensor 700.

In the temperature set mode the temperature controller 310 is arranged to control the first and second heat pump 280, 290 to bring the first and second thermal shields 260, 270 to a predetermined temperature, defined by the temperature $T_{shield}$. This mode is mainly used to bring the calorimeter 210 to the temperature at which the ITC experiments are to be run. In this mode, a first comparator block 710 compares $T_{shield}$ with the present temperature of the first shield registered by a first shield thermal sensor 720, and the output from the first comparator block 710 is directed by the mode select block 630 to the first heat pump controller 660. The second heat pump 290 is controlled in the same manner as in the isothermal mode. The thermal set mode may further be used as a stand by mode in order to keep a constant temperature in the calorimeter 210.

The temperature controller 310 may further comprise a cell temperature controller block 730 for controlling cell heating elements 740 arranged to heat the sample and the reference cells 240, 250 in accordance with a predetermined temperature set by a parameter $T_{cell}$. The cell heating elements 740, are mainly used for fine tuning of the temperature of the cells 240, 250.

The parameters $T_{shield}$, $T_{cell}$ and offset may be set via a dedicated user interface of the thermal controller, not shown, or e.g. via a calorimeter user interface run on a computer 760 or the like. Calorimetric sensors 750 for sensing the temperature difference between the sample cell 250 and reference cell 240 during the ITC experiments may be connected to the computer 760, e.g. via a preamplifier 770.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An automatic pipette assembly for an isothermal titration micro calorimetry system, comprising a pipette housing, a syringe with a titration needle arranged to be inserted into a sample cell for supplying titrant, and a linear activator for driving a plunger in the syringe, the titration needle is rotatable with respect to the housing and is provided with a stiffing paddle arranged to stir fluid in the sample cell, wherein the automatic pipette assembly comprises a stirring motor for driving the rotation of the titration needle.

2. The automatic pipette assembly of claim 1, wherein the stirring motor is a direct drive motor with a hollow rotor arranged concentric with the titration needle.

3. The automatic pipette assembly of claim 1, wherein the stirring motor drives the titration needle for rotation by a rotation transmission arrangement.

4. The automatic pipette assembly of claim 1, wherein the syringe is rotatable with respect to the housing and the titration needle is non-rotatably attached to the syringe.

5. The automatic pipette assembly of claim 4, wherein the syringe is detachably arranged in a rotation frame within the pipette housing.

6. The automatic pipette assembly of claim 1, wherein the linear activator comprises a stepper motor arranged to drive a threaded plunger, the pipette assembly further comprises position sensors for detecting two predetermined positions of the threaded plunger.

7. An isothermal titration micro calorimetry system comprising the automatic pipette assembly of claim 1.

8. The isothermal titration micro calorimetry system of claim 7, further comprising a pipette controller arranged to control the linear activator and the stirring motor of the pipette assembly, wherein the linear activator comprises a stepper motor arranged to drive a threaded plunger, the pipette assembly further comprises position sensors for detecting two predetermined positions of the threaded plunger, and wherein the pipette controller is arranged to register the two predetermined positions of the threaded plunger and to determine the pitch of the threads of the plunger from the number of steps performed by the stepper motor to move the threaded plunger between said positions.

9. A micro titration calorimetry system comprising an automatic pipette assembly with a titration needle arranged to be inserted into a sample cell for supplying titrant, and a pipette guiding mechanism arranged to guide the pipette assembly between and into at least two positions of operation, wherein a first position of operation is a pipette washing position wherein the titration needle is inserted in a washing apparatus, and a second position of operation is a titration position wherein the syringe is inserted into the sample cell for calorimetric measurements.

10. The micro titration calorimetry system of claim 9, wherein the washing apparatus is arranged to allow filling of titrant to the pipette assembly after washing of the pipette assembly is completed.

11. The micro titration calorimetry system of claim 9, further comprising a third position of operation in the form of a titrant filling position, wherein the titration needle is inserted in a titrant source.

12. The micro titration calorimetry system of claim 9, wherein the guiding mechanism is of rotational type, and the positions of operation are arranged at equal distance about the centre of rotation of the guide assembly but at different angular positions, wherein movement of the pipette assembly in the vertical direction is restricted to the angular positions of the positions of operation, and wherein rotational movement of the pipette assembly between the angular positions only is permitted when the needle is fully retracted from respective positions of operation.

13. The micro titration calorimetry system of claim 9, further comprising a position sensor arranged to register when the pipette assembly is positioned at one of the positions of operation, and wherein the associated operation is restricted by the state of the position sensor.

\* \* \* \* \*